(12) United States Patent
Kaminsky et al.

(10) Patent No.: US 6,410,661 B1
(45) Date of Patent: Jun. 25, 2002

(54) STEREORIGID METALLOCENE COMPOUNDS

(75) Inventors: Walter Kaminsky, Pinneberg; Frank Kueber, Oberursel; Berthold Schiemenz, Frankfurt; Ralf Werner, Hamburg; Anne-Meike Schauwienold, Hamburg; Frank Freidanck, Hamburg, all of (DE)

(73) Assignee: Basell Polyolefine GmbH, Kehl (DE)

( * ) Notice: Subject to any disclaimer, the term of this patent is extended or adjusted under 35 U.S.C. 154(b) by 0 days.

(21) Appl. No.: 09/423,115

(22) PCT Filed: May 6, 1998

(86) PCT No.: PCT/EP98/02671

§ 371 (c)(1),
(2), (4) Date: Nov. 2, 1999

(87) PCT Pub. No.: WO98/50395

PCT Pub. Date: Nov. 12, 1998

(30) Foreign Application Priority Data

May 6, 1997 (DE) .......................... 197 19 103

(51) Int. Cl.$^7$ .................................. C08F 4/44
(52) U.S. Cl. .................. 526/127; 526/159; 526/160; 526/348.2; 526/348.5; 526/348.6; 520/103; 520/117; 520/152
(58) Field of Search ................ 526/127, 159, 526/160, 348.2, 348.5, 348.6; 502/103, 117, 152

(56) References Cited

U.S. PATENT DOCUMENTS 5,324,801 A  6/1994  Brekner et al.

FOREIGN PATENT DOCUMENTS

| EP | 129 368 | 12/1984 |
|----|---------|---------|
| EP | 316 155 | 5/1989 |
| EP | 351 392 | 1/1990 |
| EP | 485 823 | 5/1992 |
| EP | 503 422 | 9/1992 |
| EP | 530 647 | 3/1993 |
| EP | 786 466 | * 7/1997 |

OTHER PUBLICATIONS

Alt et al. (Journal of Organometallic Chemistry, 514 (1996) pp. 257–270).*

J. Organometallic Chem. Conf. S. 136.

Chem. Lett. 1989, S. 1853–1856.

* cited by examiner

*Primary Examiner*—David W. Wu
*Assistant Examiner*—William K Cheung
(74) *Attorney, Agent, or Firm*—Keil & Weinkauf

(57) ABSTRACT

A stereorigid metallocene compound contains, as ligands, an aryl-substituted cyclopentadienyl radical, linked via a hydrogen bridge, and a substituted or unsubstituted fluorenyl radical. The novel metallocene compound is suitable as a catalyst component for olefin polymerization.

13 Claims, No Drawings

STEREORIGID METALLOCENE COMPOUNDS

The present invention relates to special stereorigid metallocene compounds and a process for the preparation of polyolefins in the presence of these special stereorigid metallocene compounds.

The literature discloses the preparation of polyolefins using soluble metallocene compounds in combination with aluminoxanes or other cocatalysts which, owing to their Lewis acidity, can convert the neutral metallocene into a cation and stabilize it (EP 129 368, EP 351 392).

The conference volume of the 1st Journal of organometallic Chemistry Conference on Applied Organometallic Chemistry, page 136, describes metallocenes which have a substituted tricyclic hydrocarbon as a ligand system.

The use of soluble metallocene compounds based on bis(cyclopentadienyl)zirconiumdialkyl or bis(cyclopentadienyl)zirconium dihalide in combination with oligomeric aluminoxanes gives atactic polymers which, owing to their unbalanced and inadequate product properties, are only of little importance industrially. Moreover, certain olefin copolymers are not obtainable.

Derivatives of zirconocene dichloride in which the two substituted cyclopentadienyl groups are linked to one another via a methylene, ethylene or dimethylsilylene bridge can, owing to their conformational rigidity, be used as catalysts for the isospecific polymerization of olefins (Chem. Lett. (1989), 1853 to 1856 or EP A 0 316 155). Metallocenes having (substituted) indenyl radicals as ligands are of particular importance for the preparation of highly isotactic polymers having high crystallinity and a high melting point (EP 485 823, EP 530 647).

Also of major interest are polyolefins whose property profile is between these two extremes.

It is an object of the present invention to provide a metallocene compound which avoids the disadvantages of the prior art and is suitable for the preparation of polyolefins.

We have found that this object is achieved by a stereorigid metallocene compound of the formula I

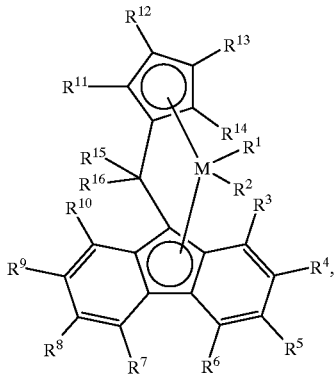

(I)

where

M is a metal of Group IIIb, IVb, Vb or VIb of the Periodic Table of the Elements, $R^1$ and $R^2$ are identical or different and are each hydrogen, a $C_1$–$C_{40}$-hydrocarbon-containing group, such as $C_1$–$C_{10}$-alkyl, $C_1$–$C_{10}$-alkoxy, $C_6$–$C_{10}$-aryl, $C_6$–$C_{25}$-aryloxy, $C_2$–$C_{10}$-alkenyl, $C_7$–$C_{40}$-arylalkyl or $C_7$–$C_{40}$-arylalkenyl, OH, halogen or $NR^{15}_2$ where $R^{15}$ is halogen, $C_1$–$C_{10}$-alkyl or $C_6$–$C_{10}$-aryl, or $R^1$ and $R^2$, together with the atoms linking them, form a ring system, $R^3$, $R^4$, $R^5$, $R^6$, $R^7$, $R^8$, $R^9$, $R^{10}$, $R^{11}$, $R^{14}$, $R^{15}$ and $R^{16}$ are identical or different and are each hydrogen, a $C_1$–$C_{40}$-hydrocarbon-containing-group, such as $C_1$–$C_{10}$-alkyl, which may be halogenated, $C_6$–$C_{30}$-aryl, which may be halogenated, $C_6$–$C_{20}$-aryloxy, $C_2$–$C_{12}$-alkenyl, $C_7$–$C_{40}$-arylalkyl, $C_7$–$C_{40}$-alkylaryl or $C_8$–$C_{40}$-arylalkenyl, halogen, $SiR^{17}_3$, $NR^{17}_2$, $SiOR^{17}_3$, $SiSR^{17}_3$ or $PR^{17}_2$, where $R^{17}$ are identical or different and are each halogen, $C_1$–$C_{10}$-alkyl or $C_6$–$C_{10}$-aryl or form a ring system, or two or more neighboring radicals $R^3$, $R^4$, $R^5$, $R^6$, $R^7$, $R^8$, $R^9$, $R^{10}$, $R^{11}$, $R^{14}$, $R^{15}$ and $R^{16}$, together with the atoms linking them, form a ring system which preferably contains 4 to 40, particularly preferably 6 to 20, carbon atoms, and $R^{12}$ and $R^{13}$ are identical or different and are each hydrogen, a $C_6$–$C_{30}$-aryl-containing group, such as $C_6$–$C_{30}$-aryl, $C_6$–$C_{20}$-aryloxy, $C_7$–$C_{40}$-arylalkyl or $C_8$–$C_{40}$-arylalkenyl, each of which may be halogenated, and at least one of the radicals $R^{12}$ and $R^{13}$ is not hydrogen.

In compounds of the formula I

M is preferably a metal of Group IVb of the Periodic Table of the Elements, such as titanium, zirconium or hafnium, in particular zirconium, $R^1$ and $R^2$ are identical and are each $C_1$–$C_4$-alkyl or halogen, such as fluorine, chlorine, bromine or iodine, in particular chlorine, $R^3$, $R^4$, $R^5$, $R^6$, $R^7$, $R^8$, $R^9$, $R^{10}$, $R^{11}$, $R^{14}$, $R^{15}$ and $R^{16}$ are identical or different and are each hydrogen, $C_1$–$C_{10}$-alkyl or $C_6$–$C_{24}$-aryl, or two or more neighboring radicals $R^3$, $R^4$, $R^5$, $R^6$, $R^7$, $R^8$, $R^9$, $R^{10}$, $R^{11}$, $R^{14}$, $R^{15}$ and $R^{16}$, together with the atoms linking them, form an aromatic or aliphatic ring system of 4 to 20 carbon atoms, and $R^{12}$ and $R^{13}$ are identical or different and are each hydrogen or $C_6$–$C_{24}$-aryl and at least one of the radicals $R^{12}$ and $R^{13}$ is not hydrogen.

Compounds of the formula I where

M is zirconium, $R^1$ and $R^2$ are identical and are each halogen, in particular chlorine, $R^3$, $R^4$, $R^5$, $R^6$, $R^7$, $R^8$, $R^9$, $R^{10}$, $R^{11}$, $R^{14}$, $R^{15}$ and $R^{16}$ are identical or different and are each hydrogen, $C_1$–$C_4$-alkyl, such as methyl, ethyl, propyl, isopropyl, butyl, tert-butyl or isobutyl, or $C_6$–$C_{14}$-aryl, such as phenyl or naphthyl, or $R^{11}$ and $R^{15}$ form a ring system, and $R^{12}$ is hydrogen and $R^{13}$ is $C_6$–$C_{14}$-aryl, are particularly preferred.

Examples of novel metallocene compounds are:

[4-($h^5$-Fluorenyl)-4,6,6-trimethyl-2-phenyl-$h^5$-tetrahydropentalene]dichlorozirconium

[Isopropylidene-(2-phenyl-$\eta^5$-cyclopentadienyl)-(9-fluorenyl)]-dichlorozirconium

[4-($h^5$-Fluorenyl)-4,6,6-trimethyl-2-phenyl-$h^5$-tetrahydropentalene]dichlorotitanium

[Isopropylidene-(2-phenyl-$\eta^5$-cyclopentadienyl)-(9-fluorenyl)]-dichlorotitanium

[4-($h^5$-Fluorenyl)-4,6,6-trimethyl-2-phenyl-$h^5$-tetrahydropentalene]dichlorohafnium

[Isopropylidene-(2-phenyl-$\eta^5$-cyclopentadienyl)-(9-fluorenyl)]-dichlorohafnium

[4-($h^5$-Fluorenyl)-4,6,6-trimethyl-2-phenyl-$h^5$-tetrahydropentalene]bisdimethylaminozirconium

[Isopropylidene-(2-phenyl-$\eta^5$-cyclopentadienyl)-(9-fluorenyl)]bisdimethylaminozirconium

[4-($h^5$-Fluorenyl)-4,6,6-trimethyl-2-(p-tolyl)-$h^5$-tetrahydropentalene]dichlorozirconium

[Isopropylidene-(2-(p-tolyl)-η⁵-cyclopentadienyl)-(9-fluorenyl)]-dichlorozirconium
[4-(h⁵-Fluorenyl)-4,6,6-trimethyl-2-(m-tolyl)-h⁵-tetrahydropentalene]dichlorozirconium
[Isopropylidene-(2-(m-tolyl)-η⁵-cyclopentadienyl)-(9-fluorenyl)]-dichlorozirconium
[4-(h⁵-Fluorenyl)-4,6,6-trimethyl-2-(o-tolyl)-h⁵-tetrahydropentalene]dichlorozirconium
[Isopropylidene-(2-(o-tolyl)-η⁵-cyclopentadienyl)-(9-fluorenyl)]-dichlorozirconium
[4-(h⁵-Fluorenyl)-4,6,6-trimethyl-2-(2,3-dimethylphenyl)-h⁵-tetrahydropentalene]dichlorozirconium
[Isopropylidene-(2-(2,3-dimethylphenyl)-η⁵-cyclopentadienyl)-(9-fluorenyl)]dichlorozirconium
[4-(h⁵-Fluorenyl)-4,6,6-trimethyl-2-(2,4-dimethylphenyl)-h⁵-tetrahydropentalene]dichlorozirconium
[Isopropylidene-(2-(2,4-dimethylphenyl)-η⁵-cyclopentadienyl)-(9-fluorenyl)]dichlorozirconium
[4-(h⁵-Fluorenyl)-4,6,6-trimethyl-2-(2,6-dimethylphenyl)-h⁵-tetrahydropentalene]dichlorozirconium
[Isopropylidene-(2-(2,6-dimethylphenyl)-η⁵-cyclopentadienyl)-(9-fluorenyl)]dichlorozirconium
[4-(h⁵-Fluorenyl)-4,6,6-trimethyl-2-(3,5-dimethylphenyl)-h⁵-tetrahydropentalene]dichlorozirconium
[Isopropylidene-(2-(3,5-dimethylphenyl)-η⁵-cyclopentadienyl)-(9-fluorenyl)]dichlorozirconium
[4-(h⁵-Fluorenyl)-4,6,6-trimethyl-2-tetramethylphenyl-h⁵-tetrahydropentalene]dichlorozirconium
[Isopropylidene-(2-tetramethylphenyl-η⁵-cyclopentadienyl)-(9-fluorenyl)]dichlorozirconium
[4-(h⁵-Fluorenyl)-4,6,6-trimethyl-2-tetramethylphenyl-h⁵-tetrahydropentalene]dichlorozirconium
[Isopropylidene-(2-tetramethylphenyl-η⁵-cyclopentadienyl)-(9-fluorenyl)]dichlorozirconium
[4-(h⁵-Fluorenyl)-4,6,6-trimethyl-2-(2,4-dimethoxyphenyl)-h⁵-tetrahydropentalene]dichlorozirconium [Isopropylidene-(2-(2,4-dimethoxyphenyl)-n⁵-cyclopentadienyl)-(9-fluorenyl)]dichlorozirconium
[4-(h⁵-Fluorenyl)-4,6,6-trimethyl-2-(3,5-dimethoxyphenyl)-h⁵-tetrahydropentalene]dichlorozirconium
[Isopropylidene-(2-(3,5-dimethoxyphenyl)-η⁵-cyclopentadienyl)-(9-fluorenyl)]dichlorozirconium,
[Isopropylidene-(2-(2,3-dimethoxyphenyl)-η⁵-cyclopentadienyl)-(9-fluorenyl)]dichlorozirconium,
[Isopropylidene-(2-(2,6-dimethoxyphenyl)-η⁵-cyclopentadienyl)-(9-fluorenyl)]dichlorozirconium
[4-(h⁵-Fluorenyl)-4,6,6-trimethyl-2-(chlorophenyl)-h⁵-tetrahydropentalene]dichlorozirconium
[Isopropylidene-(2-(chlorophenyl)-η⁵-cyclopentadienyl)-(9-fluorenyl)]dichlorozirconium
[4-(h⁵-Fluorenyl)-4,6,6-trimethyl-2-(dichlorophenyl)-h⁵-tetrahydropentalene]dichlorozirconium
[Isopropylidene-(2-(dichlorophenyl)-η⁵-cyclopentadienyl)-(9-fluorenyl)]dichlorozirconium
[4-(h⁵-Fluorenyl)-4,6,6-trimethyl-2-(trichlorophenyl)-h⁵-tetrahydropentalene]dichlorozirconium
[Isopropylidene-(2-(trichlorophenyl)-η⁵-cyclopentadienyl)-(9-fluorenyl)]dichlorozirconium
[4-(h⁵-Fluorenyl)-4,6,6-trimethyl-2-(fluorophenyl)-h⁵-tetrahydropentalene]dichlorozirconium
[Isopropylidene-(2-(fluorophenyl)-η⁵-cyclopentadienyl)-(9-fluorenyl)]dichlorozirconium
[4-(h⁵-Fluorenyl)-4,6,6-trimethyl-2-(difluorophenyl)-h⁵-tetrahydropentalene]dichlorozirconium
[Isopropylidene-(2-(difluorophenyl)-η⁵-cyclopentadienyl)-(9-fluorenyl)]dichlorozirconium
[4-(h⁵-Fluorenyl)-4,6,6-trimethyl-2-(pentafluorophenyl)-h⁵-tetrahydropentalene]dichlorozirconium
[Isopropylidene-(2-(pentafluorophenyl)-η⁵-cyclopentadienyl)-(9-fluorenyl)]dichlorozirconium
[4-(h⁵-Fluorenyl)-4,6,6-trimethyl-2-(3,5-trifluoromethyl-phenyl)-h⁵-tetrahydropentalene]dichlorozirconium
[Isopropylidene-(2-(3,5-trifluoromethyl-phenyl)-η⁵-cyclopentadienyl)-(9-fluorenyl)]dichlorozirconium
[4-(h⁵-Fluorenyl)-4,6,6-trimethyl-2-(tert-butyl-phenyl)-h⁵-tetrahydropentalene]dichlorozirconium
[Isopropylidene-(2-(tert-butylphenyl)-η⁵-cyclopentadienyl)-(9-fluorenyl)]dichlorozirconium
[4-(h⁵-Fluorenyl)-4,6,6-trimethyl-2-(3,5-di-tert-butylphenyl)-h⁵-tetrahydropentalene]dichlorozirconium
[Isopropylidene-(2-(3,5-di-tertbutylphenyl)-η⁵-cyclopentadienyl)-(9-fluorenyl)]dichlorozirconium
[4-(h⁵-Fluorenyl)-4,6,6-trimethyl-2-(biphenyl)-h⁵-tetrahydropentalene]dichlorozirconium
[Isopropylidene-(2-(biphenyl)-η⁵-cyclopentadienyl)-(9-fluorenyl)]dichlorozirconium
[4-(h⁵-Fluorenyl)-4,6,6-trimethyl-2-(biphenyl)-h⁵-tetrahydropentalene]dichlorozirconium
[Isopropylidene-(2-(biphenyl)-η⁵-cyclopentadienyl)-(9-fluorenyl)]dichlorozirconium
[4-(h⁵-Fluorenyl)-4,6,6-trimethyl-2-(3,5-diphenyl-phenyl)-h⁵-tetrahydropentalene]dichlorozirconium
[Isopropylidene-(2-(3,5-diphenyl-phenyl)-η⁵-cyclopentadienyl)-(9-fluorenyl)]dichlorozirconium
[4-(h⁵-Fluorenyl)-4,6,6-trimethyl-2-naphthyl-h⁵-tetrahydropentalene]dichlorozirconium
[Isopropylidene-(2-naphthyl-η⁵-cyclopentadienyl)-(9-fluorenyl)]dichlorozirconium The nomenclature of the abovementioned novel compound is to be illustrated on the basis of the compound [4-(h⁵-fluorenyl)-4,6,6-trimethyl-2-phenyl-h⁵-tetrahydropentalene]dichlorozirconium.

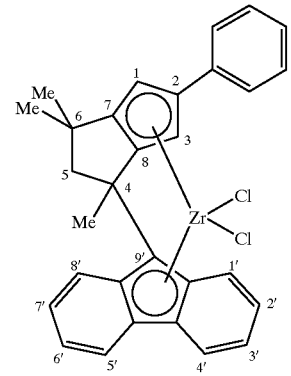

The novel metallocenes are highly active catalyst components for olefin polymerization. Depending on the substitution pattern of the ligands, the metallocenes may be obtained as an isomer mixture. The metallocenes are preferably used in the form of the pure isomer. The use of the racemate is sufficient in most cases.

However, it is also possible to use the pure enantiomer in the (+) or (−) form. An optically active polymer can be prepared using the pure enantiomers. However, the configurational isomers of the metallocenes should be separated since the polymerization-active center (the metal atom) in these compounds produces a polymer having different properties. This may be entirely desirable for specific applications, for example soft moldings.

The present invention also relates to a process for the preparation of a polyolefin by polymerizing at least one olefin in the presence of a catalyst which contains at least one cocatalyst and at least one stereorigid metallocene compound of the formula I. The term polymerization is understood as meaning homopolymerization as well as copolymerization.

One or more olefins of the formula $R^a$—CH=CH—$R^b$, where $R^a$ and $R^b$ are identical or different and are each hydrogen or a hydrocarbon radical of 1 to 20, in particular 1 to 10, carbon atoms, and $R^a$ and $R^b$, together with the atoms linking them, may form one or more rings, are preferably polymerized in the novel process. Examples of such olefins are 1-olefins of 2 to 40, preferably 2–10 carbon atoms, such as ethylene, propylene, 1-butene, 1-pentene, 1-hexene, 4-methyl-1-pentene or 1-octene, styrene, dienes, such as 1,3-butadiene, isoprene, 1,4-hexadiene or cyclic olefins.

In the novel process, preferably ethylene or propylene is homopolymerized, or ethylene is copolymerized with one or more cyclic olefins, such as norbornenes, and/or with one or more acyclic 1-olefins of 3 to 20 carbon atoms, such as propylene, and/or with one more dienes of 4 to 20 carbon atoms, such as 1,3-butadiene or 1,4-hexadiene. Examples of such copolymers are ethylene/norbornene copolymers, ethylene/propylene copolymers and ethylene/propylene/1,4-hexadiene copolymers.

The polymerization is carried out at from 60 to 250° C., particularly preferably from 50 to 200° C. The pressure is preferably from 0.5 to 2000, particularly preferably from 5 to 64, bar.

The polymerization can be carried out by solution, mass, suspension or gas-phase polymerization, continuously or batchwise, in one or more stages. A preferred embodiment is the gas-phase or solution polymerization.

The catalyst used in the novel process preferably contains a metallocene compound. It is also possible to use mixtures of two or more metallocene compounds, for example for the preparation of polyolefins having a broad or multimodal molar mass distribution.

In principle, every compound which, owing to its Lewis acidity, is capable of converting a neutral metallocene into a cation and stabilizing it is suitable as a cocatalyst in the novel process (labile coordination). In addition, the cocatalyst or the anion formed from it should not undergo any further reactions with the metallocene cation formed (EP 427 697). A preferably used cocatalyst is an aluminum compound and/or a boron compound.

The boron compound is preferably of the formula $R^{18}_x NH_{4-x} BR^{19}_4$, $R^{18}_x PH_{4-x} BR^{19}_4$, $R^{18}_3 CBR^{19}_4$ or $BR^{19}_3$, where x is from 1 to 4, preferably 3, the radicals $R^{18}$ are identical or different, preferably identical, and are each $C_1$–$C_{10}$-alkyl or $C_6$–$C_{18}$-aryl, or two radicals $R^{18}$, together with the atom linking them, form a ring, and the radicals $R^{19}$ are identical or different, preferably identical, and are each $C_6$–$C_{18}$-aryl which may be substituted by alkyl, haloalkyl or fluorine. In particular, $R^{18}$ is ethyl, propyl, butyl or phenyl and $R^{19}$ is phenyl, pentafluorophenyl, 3,5-bistrifluoromethylphenyl, mesityl, xylyl or tolyl (EP 277 003, EP 277 004 and EP 426 638).

A preferably used cocatalyst is an aluminum compound, such as aluminoxane and/or an aluminum alkyl.

A particularly preferably used cocatalyst is an aluminoxane, in particular of the formula IIa for the linear type and/or of the formula IIb for the cyclic type,

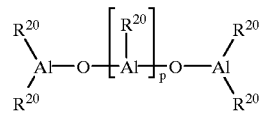 (IIa)

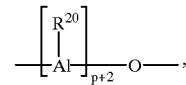 (IIb)

where, in the formulae IIa and IIb, the radicals $R^{20}$ are identical or different and are each hydrogen or a $C_1$–$C_{20}$-hydrocarbon group, such as $C_1$–$C_{,8}$-alkyl, $C_6$–$C_{18}$-aryl or benzyl, and p is an integer from 2 to 50, preferably from 10 to 35.

Preferably, the radicals $R^{20}$ are identical and are each hydrogen, methyl, isobutyl, phenyl or benzyl, particularly preferably methyl.

If the radicals $R^{20}$ are different, they are preferably methyl and hydrogen or alternatively methyl and isobutyl, hydrogen or isobutyl preferably being present in a numerical proportion of from 0.01 to 40% (of the radicals $R^{20}$).

Processes for the preparation of the aluminoxanes are known. The exact three-dimensional structure of the aluminoxanes is not known (J. Am. Chem. Soc. 115 (1993), 4971).

For example, it is possible that chains and rings link to form larger two-dimensional or three-dimensional structures.

Regardless of the method of preparation, the common feature of all aluminoxane solutions is the varying content of unconverted aluminum starting compound, which is present in free form or as an adduct.

It is possible to preactivate the metallocene compound with a cocatalyst, in particular an aluminoxane, before use in the polymerization reaction. This substantially increases the polymerization activity. The preactivation of the metallocene compound is preferably carried out in solution. Preferably, the metallocene compound is dissolved in a solution of the aluminoxane in an inert hydrocarbon. A suitable inert hydrocarbon is an aliphatic or aromatic hydrocarbon. Toluene is preferably used.

The concentration of the aluminoxane in the solution is from about 1% by weight to the saturation limit, preferably from 5 to 30% by weight, based in each case on the total amount of solution. The metallocene can be used in the same concentration but is preferably used in an amount of from $10^{-4}$ to 1 mol per mol of aluminoxane. The preactivation time is from 5 minutes to 60 hours, preferably from 5 to 60 minutes. A temperature of from 78 to 100° C., preferably from 0 to 80° C., is employed.

The metallocene compound is preferably used in a concentration, based on the transition metal, of from $10^{-3}$ to $10^{-8}$, preferably from $10^{-4}$ to $10^{-7}$, mol of transition metal per $dm^3$ of solvent or per $dm^3$ of reactor volume. The aluminoxane is preferably used in a concentration of from $10^{-6}$ to $10^{-1}$, preferably from $10^{-5}$ to $10^{-2}$, mol per $dm^3$ of solvent or per $dm^3$ of reactor volume. The other cocatalysts mentioned are used in roughly equimolar amounts, based on the metallocene compound. However, higher concentrations are in principle also possible.

The aluminoxane can be prepared in various ways by known processes. One of the methods comprises, for example, reacting an aluminum-hydrocarbon compound and/or a hydridoaluminum-hydrocarbon compound with water (in gaseous, solid, liquid or bound form—for example as water of crystallization) in an inert solvent (for example toluene). For the preparation of an aluminoxane having different radicals $R^{20}$, for example, two different trialkylaluminums are reacted with water according to the desired composition.

For removing catalyst poisons present in the olefin, purification with an aluminum compound, preferably an aluminum alkyl, such as trimethylaluminum or triethylaluminum, is advantageous. Either this purification can be carried out in the polymerization system itself or the olefin is brought into contact with the aluminum compound and then separated again before being added to the polymerization system.

In the novel process, hydrogen may be added as a molar mass regulator and/or for increasing the catalyst activity. Low molecular weight polyolefins, such as waxes, can be obtained as a result.

In the novel process, the metallocene compound is preferably reacted with the cocatalyst outside the polymerization reactor in a separate step using a suitable solvent. A catalyst carrier may be provided.

In the novel process, prepolymerization can be carried out with the aid of the metallocene compound. The olefin (or one of the olefins) used in the polymerization is preferably used for the prepolymerization.

The catalyst used in the novel process may be supported. By providing a catalyst carrier, it is possible, for example, to control the particle morphology of the polyolefin prepared. The metallocene compound can be reacted first with the carrier and then with the cocatalyst. It is also possible first to apply the cocatalyst to a carrier and then to react it with the metallocene compound. It is also possible to apply the reaction product of metallocene compound and cocatalyst to a carrier. Suitable carrier materials are, for example, silica gels, aluminas, solid aluminoxane or other inorganic carrier materials, for example magnesium chloride. Another suitable carrier material is a polyolefin powder in finely divided form. The preparation of the supported cocatalyst can be carried out, for example, as described in EP 567 952.

Preferably, the cocatalyst, e.g. aluminoxane, is applied to a carrier, for example a silica gel, an alumina, a solid aluminoxane, another inorganic carrier material or a polyolefin powder in finely divided form, and then reacted with the metallocene.

The inorganic carriers used may be oxides which were produced by flame pyrolysis, by combustion of element halides in an oxyhydrogen flame, or which can be prepared as silica gels in specific particle size distributions and particle shapes.

The preparation of the supported cocatalyst can be carried out, for example as described in EP 578 838, in the following manner in an explosion-proof stainless steel reactor having a pumping system for a pressure level of 60 bar, an inert gas supply, thermostating by jacket cooling and a second cooling circulation via a heat exchanger in the pumping system. The pumping system sucks in the reactor content via a connection in the reactor bottom by means of a pump and forces said content into a mixer and thorugh a riser tube, via a heat exchanger back into the reactor. The mixture is designed so that the feed contains a constricted pipe cross-section where a higher flow rate results and into whose turbulence zone a thin feed line is led axially and opposite to the direction of flow, through which feed line a defined amount of water can be fed in under 40 bar argon at regular intervals. The reaction is monitored by means of a sampler in the pumped circulation.

However, other reactors are in principle also suitable.

5 $dm^3$ of decane are initially taken under inert conditions in the reactor described above and having a volume of 16 $dm^3$. 0.5 $dm^3$ (=5.2 mol) of trimethylaluminum are fed in at 25° C. Thereafter, 250 g of silica gel SD 3216 30 (Grace AG), which was dried beforehand at 120° C. in an argon fluidized bed, are metered into the reactor through a solids hopper and homogeneously distributed with the aid of the stirrer and of the pumping system. A total amount of 76.5 g of water is fed into the reactor in portions of 0.1 $cm^3$ every 15 seconds in the course of 3.25 hours. The pressure, generated by the argon and the gases evolved, is kept constant at 10 bar by a pressure relief valve. After all the water has been introduced, the pumping system is switched off and stirring is continued for 5 hours at 25° C.

The supported cocatalyst prepared in this manner is used as a 10% strength suspension in n-decane. The aluminum content is 1.06 mmol of Al per $cm^3$ of suspension. The solid isolated contains 31% by weight of aluminum and the suspending medium contains 0.1% by weight of aluminum.

Further possibilities for preparing a supported cocatalyst are described in EP 578 838.

The novel metallocene is then applied to the supported cocatalyst by stirring the dissolved metallocene with the supported cocatalyst. The solvent is removed and is replaced by a hydrocarbon in which both the cocatalyst and the metallocene are insoluble.

The reaction to give the supported catalyst system is carried out at from −20 to +120° C., preferably from 0 to 100° C., particularly preferably from 15 to 40° C. The metallocene is reacted with the supported cocatalyst by combining the cocatalyst as a from 1 to 40, preferably from 5 to 20, % strength by weight suspension in an aliphatic, inert suspending medium, such as n-decane, hexane, heptane or diesel oil, with a solution of the metallocene in an inert solvent, such as toluene, hexane, heptane or dichloromethane, or with the finely milled solid metallocene. Conversely, it is also possible to react a solution of the metallocene with the solid cocatalyst.

The reaction is carried out by thorough mixing, for example by stirring, at a molar $Al/M^1$ ratio of 100/1 to 10,000/1, preferably from 100/1 to 3000/1, and with a reaction time of from 5 to 120, preferably from 10 to 60, particularly preferably from 10 to 30, minutes under inert conditions.

In the course of the reaction time for the preparation of the supported catalyst system, changes in the color of the reaction mixture occur, in particular with the use of the novel metallocenes having absorption maxima in the visible range, and the progress of the reaction can be monitored on the basis of said changes in the color.

After the reaction time has expired, the supernatant solution is separated off, for example by filtration or decanting. The solid remaining behind is washed from 1 to 5 times with an inert suspending medium, such as toluene, n-decane, hexane, diesel oil or dichloromethane, to remove soluble components in the catalyst formed, in particular to remove unconverted and hence soluble metallocene.

The supported catalyst system thus prepared, in the form of a powder after drying under reduced pressure or still in contact with the solvent, can be resuspended and metered as a suspension in one of the abovementioned inert suspending media into the polymerization system.

If the polymerization is carried out as a suspension or solution polymerization, an inert solvent customary for the Ziegler low-pressure process is used. For example, an aliphatic or cycloaliphatic hydrocarbon is employed. Examples of these are propane, butane, hexane, heptane, isooctane, cyclohexane and methylcyclohexane. A gasoline fraction or hydrogenated diesel oil fraction may furthermore be used.

Toluene may also be used. Polymerization is preferably effected in the liquid monomer.

Before the addition of the catalyst, in particular of the supported catalyst system (containing the novel metallocene and a supported cocatalyst), another aluminum alkyl compound, for example trimethylaluminum, triethylaluminum, triisobutylaluminum, trioctylaluminum or isoprenylaluminum, may additionally be introduced into the reactor for rendering the polymerization system inert (for example for separating off catalyst poisons present in the olefin). This is added to the polymerization system in a concentration of from 100 to 0.01 mmol of Al per kg of reactor content. Triisobutylaluminum and triethylaluminum in a concentration of from 10 to 0.1 mmol of Al per kg of reactor content are preferred. As a result, a low molar $Al/M^1$ ratio can be chosen in the synthesis of a supported catalyst system.

If inert solvents are used, the monomers are metered in in gaseous or liquid form.

The polymerization may be of any desired duration, since the catalyst system to be used in the novel process exhibits only a slight time-dependent decline in the polymerization activity.

The special stereorigid metallocene compounds described in the present invention are suitable for the preparation of polyolefins, in particular those having reduced crystallinity, high impact strength, high transparency, high flowability at the processing temperature and a reduced melting point.

The principal uses of such polyolefins are as plasticizers and lubricant formulations, hot-melt adhesives, coatings, sealants, insulations, casting materials or sound-insulation materials.

By using hydrogen or by increasing the polymerization temperature, it is also possible to obtain polyolefins having a lower molar mass, such as waxes, whose hardness or melting point can be varied by means of the comonomer content.

Conversely, by choosing the polymerization conditions, it is also possible to prepare high molecular weight polyolefins which are suitable as thermoplastic materials. These are suitable in particular for the production of moldings, such as films, sheets or large hollow articles (e.g. pipes).

By choosing the polymerization process and the type(s) of comonomers as well as the amount(s) of comonomers, olefin copolymers having elastomeric properties, e.g. ethylene/propylene/1,4-hexadiene terpolymers, can be prepared.

The examples which follow illustrate the invention.

Organometallic compounds were prepared and handled in the absence of air and moisture, under inert argon gas (Schlenk method). Before use, all solvents required were rendered absolutely dry by boiling for several hours over a suitable drying agent and then distilling under argon.

The preparation of the α,β-unsaturated ketones and fulvenes used as starting compound was carried out by methods known from the literature (Synlett (1991) 771; J. Chem. Soc., Commun. (1986) 1694; Chem. Ber. 116, (1983) 119; Tetrahedron Lett. 23; (1982) 1447); cyclopentadiene was obtained by cracking the dimer and was stored at −35° C.

The compounds prepared were analyzed by $^1$H-NMR.

EXAMPLE 1

Preparation of Phenylcyclopentadiene 100 ml (1.2 mol) of 2-cyclopenten-1-one in 400 ml of diethyl ether are added dropwise to 2.3 mol of phenyllithium in 1000 ml of diethyl ether at −5° C. After hydrolysis and extraction of the aqueous phase with the diethyl ether, the combined organic phases are dried over sodium sulfate. After the solvent has been stripped off, 205 g of crude product are obtained. The product is heated to 180° C. for three hours in a vigorous argon stream in a 500 ml three-necked flask having a distillation attachment, argon inlet and gas inlet tube. After 18 g of water, a total of 145.4 g of phenylcyclopentadiene are distilled at 160–180° C. and $10^{-2}$ mbar.

EXAMPLE 2

Preparation of 2-phenyl-6,6-dimethylfulvene 50 ml (80 mmol) of a 1.6 molar solution of n-butyllithium in hexane are added dropwise to 10.3 g (72 mmol) of freshly distilled phenylcyclopentadiene in 150 ml of toluene at −50° C. in the course of 40 minutes. On warming up to room temperature, a colorless precipitate forms. After filtration of the solution, the precipitate is taken up in 100 ml of toluene, and 10 ml (136 mmol) of acetone in 50 ml of toluene are added at room temperature. Hydrolysis is effected with 10% strength $(NH_4)_2CO_3$ solution. After extraction of the aqueous phase with diethyl ether, the combined organic phases are dried over sodium sulfate. After the solvent has been distilled off, 5.6 (31 mmol, 43%, based on phenylcyclopentadiene) of a yellow oil solidifying in the refrigerator are obtained.

$^1$H-NMR (100 MHz, $CDCl_3$, TMS): 7.65–7.08 (5H, m, arom. protons), 6.89–6.59 (3H, m, olefin. protons), 2.15 (6H, s, methyl protons), IR (KBr, n [$cm^{-1}$]): 2956, 2927, 2906, 1639, 1444, 1355, 25 759, 692.

Mass spectrum: m/z=182 (molecular peak)

EXAMPLE 3

Preparation of 2-(3-phenylcyclopentadienyl)-2-fluorenylpropane 13.8 ml (22 mmol) of n-butyllithium in the form of a 1.6 molar solution in hexane are added dropwise to 3.7 g (22 mmol) of fluorene in 70 ml of tetrahydrofuran at −50° C. After complete addition, the mixture is heated briefly at the boil, after which 4.0 g (22 mmol) of 2-phenyl-6,6-dimethylfulvene in 15 ml of tetrahydrofuran are added dropwise at −50° C. After 16 hours, the mixture is added to 50 ml of 0.1 molar hydrochloric acid. After extraction of the aqueous phase with diethyl ether, the combined organic phases are washed in succession with $NaHCO_3$ solution and with saturated NaCl solution and dried over $Na_2SO_4$. After recrystallization three times from ethanol, 2.7 g (7.8 mmol, 36%, based on fluorene) of colorless powder are obtained.

$^1$H-NMR (100 MHz, $CDCl_3$, TMS): 7.75–7.06 (13H, m, arom. protons), 6.90–5.90 (2H, m, olefin. protons), 4.21 (1H, s, aliph. fluorene proton), 3.59–3.38 (2H, m, aliph. Cp-protons), 1.09 (6H, s, methyl protons); IR (KBr, n [cm−1]): 3036, 2965, 2931, 2873, 1446, 745.

Mass spectrum: m/z=348 (molecular peak)

EXAMPLE 4

Prepration of [isopropylidene-(3-phenylcyclopentadienyl)-9-fluorenyl]zirconium dichloride 4.2 ml (6.7 mmol) of n-butyllithium in the form of a 1.6 molar solution in hexane are added dropwise to 1.1 g (3.2 mmol) of 2-(3-phenylcyclopentadienyl)-2-fluorenylpropane in 30 ml of tetrahydrofuran at room temperature. The mixture is heated briefly at the boil after 12 hours. After the solvent has been distilled off, the precipitate is washed with 20 ml of pentane. After the pentane has been decanted, 0.74 g (3.2 mmol) of zirconium tetrachloride and 100 ml of pentane are added. The mixture is stirred for three days at room temperature. After the pentane has been decanted, the residue is extracted with methylene chloride. After the solvent has been evaporated, 530 mg (1.0 mmol, 31%, based on zirconium tetrachloride) of the product are obtained as a crystalline, red solid.

$^1$H-NMR (100 MHz, CDCl$_3$, TMS): 8.20–7.23 (13H, m, arom. protons), 6.53, 5.91–5.87 (3H, m, arom. Cp-protons), 2.44 (6H, s, methyl protons)

EXAMPLE 5

Preparation of 1-fluorenyl-1,3,3-trimethyl-5-phenyl-1,2,3,6-tetrahydropentalene

A mixture of 10.7 ml (0.15 mol) of acetone and 10.8 ml of pyrrolidine in 100 ml of methanol is stirred at room temperature for one and a half hours. 11.5 g (0.08 mol) of freshly distilled phenylcyclopentadiene in 20 ml of diethyl ether are added to this and stirred for 40 hours. All volatile components are removed under reduced pressure from an oil pump, by condensation. 8.0 g of a reddish brown oil remain. 7.0 g of crude fulvene in 25 ml of tetrahydrofuran are added dropwise to 28 mmol of fluorenyllithium in tetrahydrofuran. The mixture is stirred for eight hours at room temperature and then heated briefly at the boil. It is then added to 50 ml of 0.1 molar hydrochloric acid. After extraction of the aqueous phase with the diethyl ether, the combined organic phases are washed in succession with NaHCO$_3$ solution and with saturated NaCl solution and dried over Na$_2$SO$_4$. Recrystallization twice from ethanol gives 2.1 g (5.4 mmol, 19%, based on fluorene) of product.

$^1$H-NMR (100 MHz, CDCl$_3$, TMS): 7.32–7.01 (13H, m, arom. protons), 6.73–6.63 (1H, m, olefin. proton), 4.10 (1H, s, aliph. fluorene proton) 3.50, 3.17 (2H, m, aliph. Cp-protons), 1.79 (3H, s, methyl protons), 1.29–1.20 (2H, m, methylene protons), 1.03 (3H, s, methyl protons), 0.35 (3H, s, methyl protons), IR (KBr, n [cm-1]): 3058, 3033, 2949, 2925, 2860, 1446, 1168, 746, 693.

Mass spectrum: m/z=388 (C$_{30}$H$_{28}$, molecular peak)

EXAMPLE 6

Preparation of [4-(h$^5$-fluorenyl)-4,6,6-trimethyl-2-phenyl-h$^5$-tetrahydropentalene]dichlorozirconium 7.0 ml (11 mmol) of n-butyllithium in the form of a 1.6 molar solution in n-hexane are added dropwise to 1.5 g (3.9 mmol) of 1-fluorenyl-2,3-dihydro-1,3,3-trimethyl-5-phenylpentalene in 50 ml of tetrahydrofuran at room temperature. After stirring for 12 hours, the mixture is heated briefly at the boil and the precipitate obtained by removing the solvent by condensation is washed twice with 50 ml of pentane. After the pentane has been decanted, 1.0 g (4.3 mmol) of zirconium tetrachloride and 50 ml of pentane are added and stirring is carried out for three days at room temperature. After the pentane has been removed by condensation, the residue is extracted with methylene chloride. After the solvent has been evaporated, 350 mg (0.6 mmol, 15%, based on zirconium tetrachloride) of the product are obtained as a crystalline, red solid.

$^1$H-NMR (100 MHz, C$_2$D$_2$Cl$_4$): 7.99–7.75, 7.52–6.93 (13H, m, arom. protons), 6.31, 5.50 (2H, m, arom. Cp-protons), 3.98 (1H, d, J=15 Hz, methylene proton) 2.63 (1H, d, J=15Hz, methylene proton), 2.35 (3H, s, methyl protons), 1.40 (3H, s, methyl protons), 1.34 (3H, s, methyl protons)

Mass spectrum: m/z=548 (C$_{30}$H$_{26}$ZrCl$_2$, molecular peak with correct isotope distribution)

EXAMPLE 7

Ethylene Polymerization 100 cm$^3$ of toluene and 150 mg of a solution of methylaluminoxane in toluene (10% strength by weight methylaluminoxane solution of molar mass 1300 g/mol according to cryoscopic determination) were initially taken, in a countercurrent argon stream, in a 1 dm$^3$ glass autoclave which had been thoroughly flushed with argon and brought to the polymerization temperature (30° C.) beforehand. The solution was saturated with ethylene by forcing in ethylene (2.5 bar) several times. A solution of 5×10$^{-7}$ mol of [4-(h$^5$-fluorenyl)-4,6,6-trimethyl-2-phenyl-h$^5$-tetrahydropentalene]dichlorozirconium in 1 cm$^3$ was added in a gentle countercurrent ethylene stream.

Polymerization was carried out for one hour while stirring, the ethylene pressure being kept at 2.5 bar by further metering.

After the end of the reaction time, the ethylene was let out of the reactor and the polymerization mixture was stirred with a little ethanol. It was then discharged from the reactor and stirred overnight with a 10% strength ethanolic hydrochloric acid solution. This was followed by washing with saturated NaHCO$_3$ solution and washing twice with about 100 cm$^3$ of water. The polymer filtered off was dried at 60° C. under reduced pressure until the weight remained constant.

After drying, 0.55 g of colorless polymer which had a molar mass of 540,000 g/mol was obtained.

EXAMPLES 8–12

Ethylene Polymerization

The polymerization and working up were carried out as described in Example 7.

In contrast to Example 7, in each case 400 ml of toluene and 600 mg of a solution of methylaluminoxane in toluene (10% strength by weight methylaluminoxane solution of molar mass 1300 g/mol according to cryoscopic determination) were initially taken. The catalyst used was [isopropylidene-(3-phenylcyclopentadienyl)-9-fluorenyl] zirconium dichloride.

The details of the polymerization procedure and the results are summarized in Table 1.

TABLE 1

| Example | Ethene pressure [bar] | Reaction temperature [° C.] | Amount of catalyst [mol] | Duration of polymerization [h] | Polymer yield [g] | Molar mass [g/mol] |
|---|---|---|---|---|---|---|
| 8 | 1.54 | 0 | 8 × 10$^{-7}$ | 3.66 | 0.98 | 740,000 |
| 9 | 1.98 | 15 | 8 × 10$^{-7}$ | 1.42 | 2.90 | 750,000 |
| 10 | 2.50 | 30 | 1.6 × 10$^{-7}$ | 3.37 | 7.60 | 530,000 |
| 11 | 3.10 | 45 | 4 × 10$^{-8}$ | 1 | 2.98 | 260,000 |
| 12 | 3.57 | 60 | 4 × 10$^{-8}$ | 0.66 | 5.22 | 165,000 |

EXAMPLES 13 AND 14

Propylene Polymerization

The polymerization was carried out analogously to Example 7. In contrast to Example 7, however, in each case 200 ml of toluene and a solution of methylaluminoxane in toluene (10% strength by weight methylaluminoxane solution of molar mass 1300 g/mol according cryoscopic determination) were initially taken. The reaction pressure was kept at 2.0 bar, the polymerization temperature was 30° C. $2\times10^{-6}$ mol of the catalyst in solution in toluene were used. The duration of polymerization was 1 hour.

After the end of the reaction time, the propylene was let out of the reactor and the polymerization mixture was stirred with a little ethanol. It was then discharged from the reactor and precipitated by dropwise addition to ethanol. The polymer filtered off was dried at 60° C. under reduced pressure until the weight remained constant.

The details of the polymerization procedure and the results are summarized in Table 2.

TABLE 2

| Example | Initially taken amount of MAO [mg] | Catalyst | Polymer yield [g] | Molar mass (viscosi-metric) [g/mol] |
|---|---|---|---|---|
| 13 | 330 | [4-(h⁵-Fluorenyl)-4,6,6-trimethyl-2-phenyl-h⁵-tetrahydropentalene]-dichlorozirconium | 0,75 | |
| 14 | 300 | [Isopropylidene-(3-phenyl cyclopentadienyl)-9-fluorenyl] zirconium dichloride | 9.67 | 60,000 |

EXAMPLES 15–19

Norbornene/ethylene Copolymerization

A solution of norbornene in 200 ml of toluene and 500 mg of a solution of methylaluminoxane in toluene (10% strength by weight methylaluminoxane solution of molar mass 1300 g/mol according to cryoscopic determination) were initially taken, in a countercurrent argon stream, in a 1 dm³ glass autoclave which had been thoroughly flushed with argon and brought to the polymerization temperature (30° C.) beforehand. The solution was saturated with ethylene by forcing in ethylene (2.0 bar) several times. A solution of $5\times10^{-7}$ mol of [isopropylidene-(3-phenylcyclopentadienyl)-9-fluorenyl] zirconium dichloride in 1 cm³ was added in a gentle countercurrent ethylene stream.

Polymerization was carried out while stirring, the ethylene pressure being kept at 2.0 bar by further metering.

After the end of the reaction time, the ethylene was let out of the reactor and the polymerization mixture was stirred with a little ethanol. It was then discharged from the reactor and precipitated by dropwise addition to ethanol. The polymer filtered off was dried at 60° C. under reduced pressure until the weight remained constant.

The details of the polymerization procedure and the results are summarized in Table 3.

TABLE 3

| Example | Initially taken amount of norbornene [ml], based on a 7 N solution of norbornene in toluene | Duration of polymeri-zation [h] | Polymer yield [g] | Rate of incorpo-ration of norbornene |
|---|---|---|---|---|
| 15 | 1.7 | 0.17 | 0.69 | |
| 16 | 4.5 | 0.2 | 0.66 | |
| 17 | 10.2 | 1.08 | 1.73 | 0.19 |
| 18 | 27.3 | 2 | 1.37 | |
| 19 | 61.4 | 3 | 1.55 | 0.39 |

We claim:
1. Stereorigid metallocene compounds of the formula I,

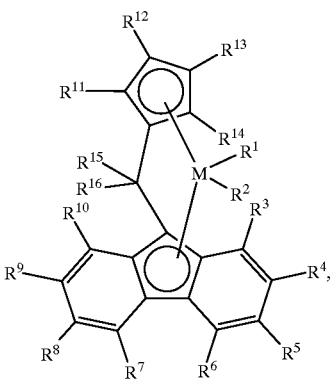

(I)

where
M is a metal of Group IIIb, IVb, Vb or VIb of the Periodic Table of the Elements,
$R^1$ and $R^2$ are identical or different and are each hydrogen, a $C_1$–$C_{40}$-hydrocarbon-containing group, OH, halogen or $NR_2$, where R is halogen, $C_1$–$C_{10}$-alkyl or $C_{6-C10}$-aryl, or $R^1$ and $R^2$ together with the atoms linking them, form a ring system (I);
$R^3$, $R^4$, $R^5$, $R^6$, $R^7$, $R^8$, $R^9$, $R^{10}$, $R^{11}$, $R^{14}$, $R^{15}$ and $R^{16}$ are identical or different and are each hydrogen, a $C_1$–$C_{40}$-hydrocarbon-containing group halogen, $SiR^{17}_3$, $NR^{17}_2$, $SiOR^{17}_3$, $SiSR^{17}_3$ or $PR^{17}_2$, where $R^{17}$ are identical or different and are each halogen, $C_1$–$C_{10}$-alkyl or $C_6$–$C_{10}$-aryl or form a ring system (2), or two or more neighboring radicals $R^3$, $R^4$, $R^5$, $R^6$, $R^7$, $R^8$, $R^9$, $R^{10}$, $R^{11}$, $R^{14}$, $R^{15}$ and $R^{16}$, together with the atoms linking them, form a ring system (3),
and $R^{12}$ and $R^{13}$ are identical or different and are each hydrogen or a $C_6$–$C_{30}$-aryl-containing group, and at least one of the radicals $R^{12}$ and $R^{13}$ is not hydrogen.
2. The stereorigid metallocene compounds of claim 1, wherein
M is a metal Group IVb of the Periodic Table of the Elements,
$R^1$ and $R^2$ are identical and are each $C_1$–$C_4$-alkyl or halogen,
$R^3$, $R^4$, $R^5$, $R^6$, $R^7$, $R^8$, $R^9$, $R^{10}$, $R^{11}$, $R^{14}$, $R^{15}$ and $R^{16}$ are identical or different and are each hydrogen, $C_1$–$C_{10}$-alkyl or $C_6$–$C_{24}$-aryl, or two or more neighboring radicals $R^3$, $R^4$, $R^5$, $R^6$, $R^7$, $R^8$, $R^9$, $R^{10}$, $R^{11}$, $R^{14}$, $R^{15}$ and $R^{16}$, together with the atoms linking them, form an aromatic or aliphatic ring system of 4 to 20 carbon atoms, and $R^{12}$ and $R^{13}$ are identical or different and are each hydrogen or $C_6$–$C_{24}$-aryl.

3. The stereorigid metallocene compounds of claim 1, wherein

M is zirconium, $R^1$ and $R^2$ are identical and are each halogen, $R^3$, $R^4$, $R^5$, $R^6$, $R^7$, $R^8$, $R^9$, $R^{10}$, $R^{11}$, $R^{14}$, $R^{15}$ and $R^{16}$ are identical or different and are each hydrogen, $C_1$–$C_4$-alkyl, $C_6$–$C_{14}$-aryl or $R^{14}$ and $R^{15}$ form a ring system.

4. A catalyst containing a) at least one stereorigid metallocene compound of claim 1 and b) at least one cocatalyst.

5. The catalyst of claim 4, where the cocatalyst is an aluminoxane.

6. The catalyst of claim 4, additionally containing a carrier.

7. A process for the preparation of a polyolefin comprising polymerizing at least one olefin in the presence of the catalyst of claim 4.

8. The process of claim 7, wherein the olefins have of the formula $R^a$—CH=Ch—$R^b$, where $R^a$ and $R^b$ are identical or different and are each hydrogen or a hydrocarbon radical of 1 to 20 carbon atoms, and $R^a$ and $R^b$, together with the atoms linking them, may from one or more rings.

9. A polyolefin obtained by the process of claim 8.

10. The metallocene compounds of claim 1 wherein the $C_1$–$C_{40}$-hydrocarbon-containing groups of $R^1$ and $R^2$ are $C_1$–$C_{10}$-alkyl, $C_1$–$C_{10}$-alkoxy, $C_6$–$C_{10}$-aryl, $C_6$–$C_{25}$-aryloxy, $C_2$–$C_{10}$-alkenyl, $C_7$–$C_{40}$-arylalkyl or $C_7$–$C_{40}$-arylalkenyl; the $C_1$–$C_{40}$-hydrocarbon-containing groups $R^3$–$R^{11}$ and $R^{14}$–$R^{16}$ are $C_1$–$C_{10}$-alkyl, which may be halogenated, $C_6$–$C_{30}$-aryl, which may be halogenated, $C_6$–$C_{20}$-aryloxy, $C_2$–$C_{12}$-alkenyl, $C_7$–$C_{40}$-arylalkyl, $C_7$–$C_{40}$-arylalkyl or $C_8$–$C_{40}$-arylalkeny, and ring system (3) contains 4–'carbon atoms.

11. The metallocene compounds of claim 10 wherein system (3) contains 6–20 carbon atoms.

12. The metallocene, compounds of claim 2 wherein M is zirconium and the $R^1$ and $R^2$ are both chlorine.

13. The metallocene compounds of claim 3 wherein $R^1$ and $R^2$ are both chlorine.

* * * * *

UNITED STATES PATENT AND TRADEMARK OFFICE
CERTIFICATE OF CORRECTION

PATENT NO.   : 6,410,661 B1
DATED        : June 25, 2002
INVENTOR(S)  : Kaminsky et al.

It is certified that error appears in the above-identified patent and that said Letters Patent is hereby corrected as shown below:

Column 14,
Line 39, "$C_6\text{-}C_{10}\text{-}$" should be -- $C_1\text{-}C_{10}\text{-}$ --.

Column 16,
Line 12, "4-carbon" should be -- 4-40 carbon --.

Signed and Sealed this

Fifteenth Day of October, 2002

Attest:

Attesting Officer

JAMES E. ROGAN
Director of the United States Patent and Trademark Office